(12) United States Patent
Coon et al.

(10) Patent No.: US 12,061,204 B2
(45) Date of Patent: Aug. 13, 2024

(54) METHOD TO MAP PROTEIN LANDSCAPES

(71) Applicant: Wisconsin Alumni Research Foundation, Madison, WI (US)

(72) Inventors: Joshua Coon, Middleton, WI (US); Harald Marx, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 21 days.

(21) Appl. No.: 17/231,977

(22) Filed: Apr. 15, 2021

(65) Prior Publication Data

US 2021/0239708 A1 Aug. 5, 2021

Related U.S. Application Data

(63) Continuation of application No. 15/988,566, filed on May 24, 2018, now abandoned.

(Continued)

(51) Int. Cl.
*G01N 33/68* (2006.01)
*G16B 30/00* (2019.01)
*G16B 30/20* (2019.01)
*G16B 40/00* (2019.01)
*G16B 40/10* (2019.01)

(Continued)

(52) U.S. Cl.
CPC ..... *G01N 33/6848* (2013.01); *G01N 33/6824* (2013.01); *G01N 33/6842* (2013.01); *G16B 30/00* (2019.02); *G16B 30/20* (2019.02); *G16B 40/00* (2019.02); *G16B 40/10* (2019.02); *G16B 40/30* (2019.02); *H01J 49/0036* (2013.01); *H01J 49/004* (2013.01); *G01N 2570/00* (2013.01)

(58) Field of Classification Search
USPC ......................................................... 436/173
See application file for complete search history.

(56) References Cited

U.S. PATENT DOCUMENTS

2006/0255258 A1 11/2006 Wang et al.
2012/0245857 A1 9/2012 Lee et al.
2018/0340941 A1 11/2018 Coon et al.

OTHER PUBLICATIONS

Hartigan et al. (1979) "A K-Means Clustering Algorithm," Applied Statistics 28:100-108.

(Continued)

*Primary Examiner* — Xiaoyun R Xu
(74) *Attorney, Agent, or Firm* — Leydig, Voit & Mayer, Ltd.

(57) ABSTRACT

In shotgun proteomics, generally only a fraction of peptides from a parent protein are actually detected. Because a large portion of the protein sequence is not detected, it is often impossible to determine whether the expressed protein is present in a modified, spliced, or truncated form. Provided herein are methods and systems for analyzing polypeptides which allow for the increase of the mean sequence coverage of a protein concomitant with bioinformatics analysis in order to distinguish putative proteoforms with improved amino acid resolution. Aspects of the invention include (1) a deep sequencing strategy to provide more protein sequence coverage than is typically achieved, and (2) a computational approach to view protein expression across its full length and identify regions of the protein that are potentially subject to such regulation. This technology has global utility in proteomics and will be of particular use for the analysis of biosimilar protein drug therapeutics.

12 Claims, 2 Drawing Sheets

Related U.S. Application Data

(60) Provisional application No. 62/511,011, filed on May 25, 2017.

(51) Int. Cl.
*G16B 40/30* (2019.01)
*H01J 49/00* (2006.01)

(56) References Cited

OTHER PUBLICATIONS

Huang et al. (2008) "Data-Mining Scheme for Identifying Peptide Structural Motifs Responsible for Different MS/MS Fragmentation Intensity Patterns," Journal of Proteome Research, vol. 7, pp. 70-79.
MacQueen, J. B. (1967) "Some Methods for Classification and Analysis of Multivariate Observations, Proceedings of 5th Berkeley Symposium on Mathematical Statistics and Probability," Berkeley, University of California Press, 1:281-297.
Tsiatsiani et al. (2015) "Proteomics beyond trypsin," FEBS Journal, vol. 282, pp. 2612-2626.
Valikangas et al. (Oct. 2016) "A systematic evaluation of normalization methods in quantitative label-free proteomics," Briefings in Bioinformatics, 19(1) 1-11.
U.S. Appl. No. 15/988,566, filed May 24, 2018.

METHOD TO MAP PROTEIN LANDSCAPES

CROSS-REFERENCE TO RELATED APPLICATIONS

This application claims priority from U.S. application Ser. No. 15/988,566, filed May 24, 2018, and from U.S. Provisional Patent Application No. 62/511,011, filed May 25, 2017, which is incorporated by reference herein to the extent that there is no inconsistency with the present disclosure.

STATEMENT REGARDING FEDERALLY SPONSORED RESEARCH OR DEVELOPMENT

This invention was made with government support under GM 118110 and GM108538 awarded by the National Institutes of Health. The government has certain rights in the invention.

BACKGROUND OF THE INVENTION

Mass-spectrometry-based proteomics is a key technology for studying the proteome, which can comprise canonical gene products, alternative gene products, post-translational modifications (PTMs), non-synonymous single nucleotide polymorphisms (SNPs) and other sequence variations. The most prevalent paradigms are top-down proteomics and bottom-up proteomics, also known as shotgun proteomics. In shotgun proteomics, proteins in a sample undergo proteolytic digestion, breaking the proteins into smaller pieces (peptides), which are then subjected to analysis by mass spectrometry. To infer the amino acid sequence and quantity of the peptides, the resulting data is often processed using a search engine in conjunction with a sequence database containing data of known peptides and proteins.

In shotgun proteomics, it is important that the digest is able to produce peptides appropriate for the mass spectrometer. The most common and effective protease is trypsin, which will cleave C-terminal to the amino acids arginine and lysine, resulting in a mean protein sequence coverage in the range of 15% to 20%. Trypsin's moderate sequence coverage is sufficient for most proteomics experiments but does not provide sufficient sequence coverage for distinguishing various forms of a protein (proteoforms). Other proteases are similar in that they only provide partial coverage of the total protein sequence.

As a result of the partial coverage provided by conventional digests, typically only a fraction of the peptides from the parent protein are actually detected and analyzed. Many modifications, splicing events, single nucleotide polymorphisms, and truncations of the proteome frequently occur and are tightly regulated. However, because the entire protein sequence is not detected, it is often impossible to determine whether the expressed protein is present in a modified, spliced, or truncated form. As such, this level of information is often not collected during conventional proteomic analyses, and there is currently no good way to monitor which form(s) of a protein exists in the cell, or which form(s) of a protein are present in a purified protein drug therapeutic.

SUMMARY OF THE INVENTION

To overcome the above limitations, the present invention discloses methods and systems for analyzing polypeptides which provide increased sequence coverage and improved analysis of the protein and proteoform. Embodiments of the invention include a deep sequencing strategy to provide more protein sequence coverage than is typically achieved by conventional means, as well as a computational approach to view protein expression across the full length of the protein to identify regions that are potentially subject to alterations, regulation, processing, and modifications.

Aspects of the invention include improved sample preparation, high resolution mass-spectrometry, bioinformatic analysis, and combinations thereof. For example, embodiments of the present invention encompass the use of multiple proteases, which allow for the increase of the mean sequence coverage (in some cases, up to 80%), concomitant with bioinformatics analysis in order to distinguish putative proteoforms with improved amino acid resolution.

In embodiments described herein, multiple samples of the same polypeptide are used to determine the sequence and proteoform information of the polypeptide with great accuracy. In some embodiments, one or more samples of different polypeptides are used to determine and compare the sequence and proteoform information of the polypeptides.

In an embodiment, the present invention provides a method for analyzing a polypeptide having an amino acid sequence. The method comprises the steps of: a) digesting a first sample of the polypeptide with a first protease or chemical agent; b) digesting a second sample of the polypeptide with a second protease or chemical agent; c) generating tandem mass spectrometry data on each digested polypeptide sample; and d) combining mass spectrometry data from each digested polypeptide sample to generate comprehensive mass spectrometry data on the polypeptide.

Optionally, the method further comprises digesting one or more additional samples of the polypeptide with one or more additional proteases or chemical agents, wherein the protease or chemical agent used for each sample is a different protease or chemical agent used to digest any other sample. For example, in an embodiment the method further comprise digesting a third sample of the polypeptide with a third protease, digesting a fourth sample of the polypeptide with a fourth protease, digesting a fifth sample of the polypeptide with a fifth protease, and/or digesting a sixth sample of the polypeptide with a sixth protease. Each protease or chemical agent used to digest a sample is different. In an embodiment, three to four samples are independently digested by three to four unique proteases. In an embodiment, each sample is digested and analyzed concurrently with the other sample, analyzed on the mass spectrometer device, and/or as part of the same experiment.

In an embodiment, the present invention provides a method for analyzing two or more polypeptides comprising the steps of: a) independently digesting a first sample of a first polypeptide and a first sample of a second polypeptide with a first protease or chemical agent; b) independently digesting a second sample of the first polypeptide and a second sample of the second polypeptide with a second protease or chemical agent; c) generating tandem mass spectrometry data on each digested polypeptide sample; d) for each polypeptide, combining mass spectrometry data from each digested polypeptide sample of that polypeptide to generate comprehensive mass spectrometry data; and e) generating at least a partial consensus amino acid sequence for each polypeptide from the comprehensive mass spectrometry data and calculating abundances of amino acids. In an embodiment, the partial consensus amino acid sequence provides at least 50% of the full length polypeptide sequence, preferably, 60% of the full length polypeptide sequence, or 80% of the full length polypeptide sequence. A further embodiment comprises f) comparing the consensus sequence abundances of amino acids of each polypeptide, and identifying differences in amino acid abundance between the polypeptides.

Optionally, the method further comprises independently digesting a third sample of the first polypeptide and a third sample of the second polypeptide with a third protease; independently digesting a fourth sample of the first polypeptide and a fourth sample of the second polypeptide with a fourth protease; independently digesting a fifth sample of the first polypeptide and a fifth sample of the second polypeptide with a fifth protease; and/or independently digesting a sixth sample of the first polypeptide and a sixth sample of the second polypeptide with a sixth protease. Each protease or chemical agent used to digest a sample is different. In an embodiment, three to four samples of each polypeptide are independently digested.

Optionally, the tandem mass spectrometry data for each digested polypeptide sample in the methods described herein is generated by first generating a distribution of precursor ions during $MS^1$ stage ionization, fragmenting precursor ions having a mass-to-charge ratio (m/z) within a selected target m/z range during $MS^2$ stage fragmentation, thereby generating a plurality of product ions where the product ions correspond to portions of the amino acid sequence of the polypeptide, and measuring the m/z and intensity of the product ions, thereby generating mass spectrometry data for each digested polypeptide sample.

In an embodiment, the comprehensive mass spectrometry data is used to generate at least a partial consensus amino acid sequence of the polypeptide. For example, the comprehensive mass spectrometry data is used to calculate the quantity or abundances of amino acids for one or more selected portions of the polypeptide, including, but not limited to, portions which comprise the N-terminus of the polypeptide. In an embodiment, the abundance or quantification of amino acids is performed without the use of an isobaric or chemical label attached to the polypeptide.

Preferably, the comprehensive mass spectrometry data provides sequence coverage for at least 20% of the full length amino acid sequence of the polypeptide, at least 30% of the full length amino acid sequence of the polypeptide at least 40% of the full length amino acid sequence of the polypeptide, at least 50% of the full length amino acid sequence of the polypeptide, at least 60% of the full length amino acid sequence of the polypeptide, at least 70% of the full length amino acid sequence of the polypeptide, or at least 80% of the full length amino acid sequence of the polypeptide.

In a further embodiment, the mass spectrometry data for different polypeptides is compared to one another to determine any differences between the polypeptide samples. These differences include the presence or absence of amino acids, polymorphisms, mutations, and post translational modification (PTMs) of amino acids, including but not limited to phosphorylation, glycosylation, ubiquitination, nitrosylation, methylation, acetylation, lipidation and proteolysis. In an embodiment, at least one sample polypeptide is a control polypeptide and least one of the other sample polypeptides is a polypeptide which has undergone a suspected modification, splice, truncation, polymorphism or mutation. In a further embodiment, the modification is a post-translational modification or the result of a single nucleotide polymorphism.

In a further embodiment, the measured intensities of the product ions from each digested polypeptide sample are normalized during generation of the comprehensive mass spectrometry data. The normalized data is then optionally used to identify a portion of the product ions as corresponding to one or more known amino acid sequence fragments of the polypeptide sample. In a further embodiment, k-means clustering analysis is performed on the normalized intensity data during generation of the comprehensive mass spectrometry data. Optionally, alternative clustering algorithms can be used to group data points.

Proteases suitable for use with the present invention include, but are not limited to, the group consisting of trypsin, Lys-N, Lys-C, Glu-C (Protease V8), chymotrypsin, Asp-N, and combinations thereof. Chemical agents suitable for use with the present invention include, but are not limited to, the group consisting of cyanogen bromide, formic acid, hydroxylamine, 2-nitro-5-thiocyanobenzoic acid (NTCB), and BNPS skatole (2-(2-nitrophenylsulfenyl)-3-methyl-3-bromoindolenine).

Preferably, the polypeptides analyzed with the methods of the present invention are antibodies, antibody-drug conjugates, or therapeutic proteins that can be administered to a subject. In an embodiment, the present methods are used to determine if therapeutic products generated during a biochemical or manufacturing process have the same quality and proteoform as a desired control antibody, antibody-drug conjugate, or therapeutic protein. For example, in an embodiment, a first analyzed polypeptide is a control therapeutic polypeptide, antibody, or antibody-drug conjugate, and a second analyzed polypeptide is a production therapeutic polypeptide, antibody, or antibody-drug conjugate made during a biochemical process or manufacturing process.

In a further embodiment, the first polypeptide is a control polypeptide produced by a cell and the second polypeptide is produced by a cell which has been administered a treatment. The polypeptides are then analyzed to determine if the treatment alters the sequence or proteoform of the polypeptide.

In an embodiment, the mass spectrometry data is generated at a resolution of 60K or greater. In another embodiment, the mass spectrometry data is generated at a resolution of 120K or greater. In another embodiment, mass spectrometry data collected from the $MS^1$ stage is generated at a resolution of 60K or greater, and mass spectrometry data collected from the $MS^2$ stage is generated at a resolution of 120K or greater.

In addition to determining the proteoform of a protein, the methods and systems described herein can also be used to determine specific amino acid abundance in addition to or instead of peptide abundance. Accordingly, the methods described herein will be greatly useful to the proteomics community, as well as to the pharmaceutical industry by allowing the full characterization of the sequence and structure of biosimilar drug therapeutics and determining quality assurance. Taking all together, these methods can impact the proteomics community and pharmaceutical industry alike.

In an embodiment, the invention also provides a system for analyzing a polypeptide having an amino acid sequence comprising: a) an ion source for generating ions from a plurality of digested samples of the polypeptide; b) ion fragmentation optics in communication with the ion source for generating product ions; c) an ion detector in communication with the ion fragmentation optics for detecting ions according to their mass-to-charge ratios; and d) a mass analyzer in communication with the ion detector. The mass analyzer comprises a software program enabling the mass analyzer to: i) measure m/z and intensity of the detected ions, thereby generating mass spectrometry data for each digested polypeptide sample; ii) normalize the measured intensities of the product ions from each digested polypeptide sample; and iii) combine mass spectrometry data from each digested polypeptide sample to generate comprehensive mass spectrometry data on the polypeptide, wherein the comprehensive mass spectrometry data provides sequence coverage for at least 20% (preferably at least 50% or 80%) of the full length amino acid sequence of the polypeptide. Optionally, the mass analyzer is able to generate at least a partial consensus amino acid sequence for the polypeptide from the comprehensive mass spectrometry data and calculate abundances of amino acids for one or more selected portions of the polypeptide from the comprehensive mass spectrometry data. In an embodiment, the mass analyzer utilizes k-means clustering analysis on the normalized intensity data to generate the comprehensive mass spectrometry data. In an embodiment, the system generates comprehensive mass spectrometry data from two or more samples, three or more samples, four or more samples, five or more samples, or six or more samples.

DETAILED DESCRIPTION OF THE INVENTION

Definitions

Figure 1:
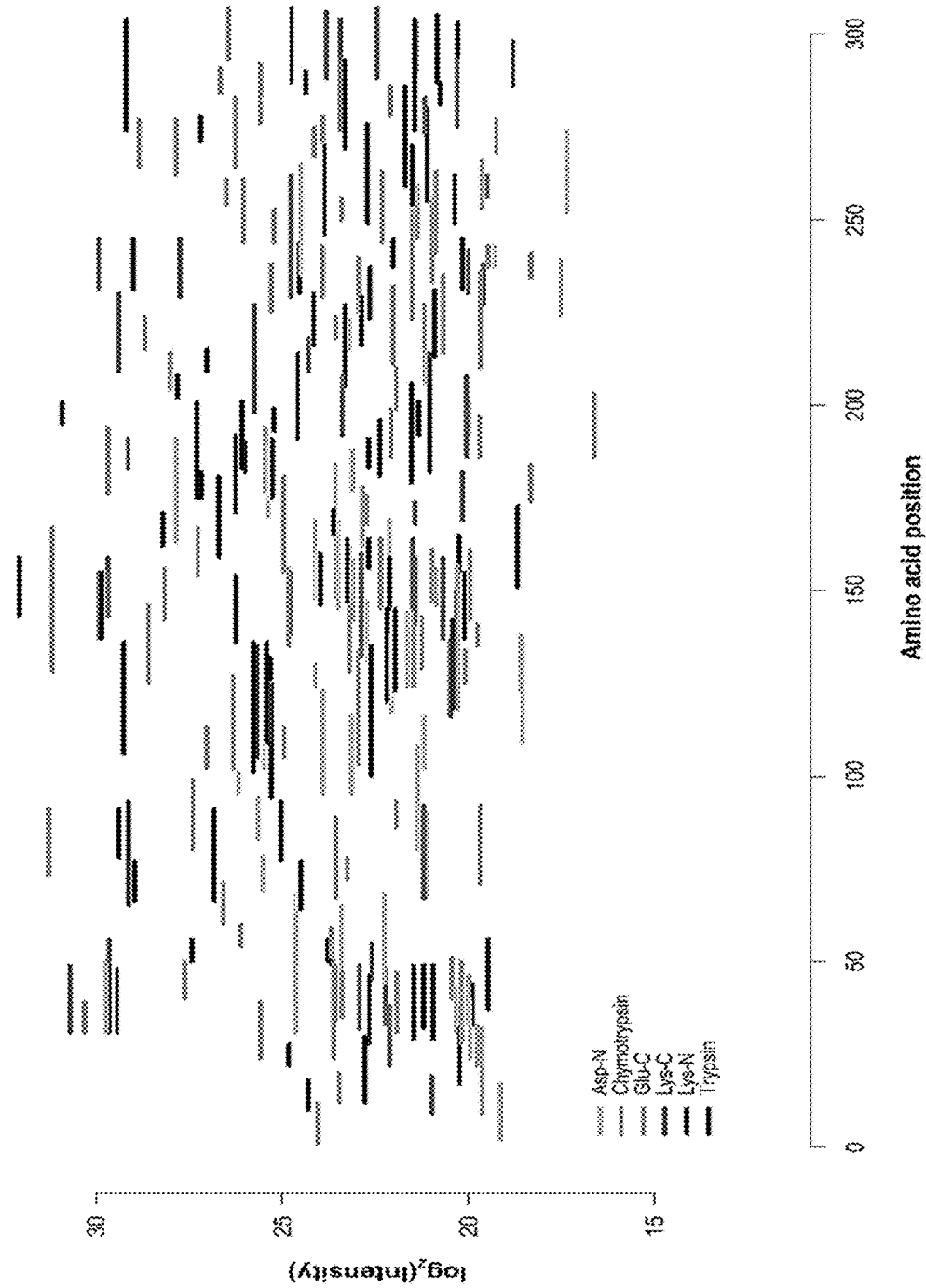
FIG. 1 illustrates peptide mapping to coenzyme Q5. Each line represents a peptide identified and quantified by mass-spectrometry based proteomics over the full sequence length of coenzyme Q5. The peptides are a product of proteolytic digestion with six proteases (Asp-N, Chymotrypsin, Glu-C, Lys-C, Lys-N, and Trypsin).

In general the terms and phrases used herein have their art-recognized meaning, which can be found by reference to standard texts, journal references and contexts known to those skilled in the art. The following definitions are provided to clarify their specific use in the context of the invention.

As used herein, the term "proteoform" refers to the specific molecular form of a protein product arising from a specific gene. The proteoform of a polypeptide encompasses not only the translated amino acid sequence of the polypeptide, but also includes post-translational modifications of the polypeptide.

Post-translational modifications (PTMs) are modifications that occur on a protein, typically catalyzed by enzymes, after its translation by ribosomes is complete. PTMS generally refer to the covalent addition of a functional group to a protein, proteolytic cleavage, or degradation of protein regions. PTMs include but are not limited to phosphorylation, glycosylation, ubiquitination, nitrosylation, methylation, acetylation, neddylation, lipidation and proteolysis.

As used herein, the term "mass spectrometry" (MS) refers to an analytical technique for the determination of the elemental composition of an analyte. Mass spectrometric techniques are useful for elucidating the chemical structures of analytes, such as peptides and other chemical compounds. The mass spectrometry principle consists of ionizing analytes to generate charged species or species fragments and measurement of their mass-to-charge ratios. Conducting a mass spectrometric analysis of an analyte results in the generation of mass spectrometry data relating to the mass-to-charge ratios of the analyte and analyte fragments. Mass spectrometry data corresponding to analyte ion and analyte ion fragments is presented in mass-to-charge (m/z) units representing the mass-to-charge ratios of the analyte ions and/or analyte ion fragments. In tandem mass spectrometry (MS/MS), multiple rounds of mass spectrometry analysis are performed. For example, during the $MS^1$ stage of tandem Mass spectrometry, samples containing a mixture of proteins and peptides are ionized and the resulting precursor ions scanned to determine their mass-to-charge ratio. During the $MS^2$ stage, selected precursor ions are fragmented and further analyzed according to the mass-to-charge ratio of the fragments.

As used herein, the term "mass-to-charge ratio" refers to the ratio of the mass of a species to the charge state of a species.

As used herein, the term "precursor ion" is used herein to refer to an ion which is produced during ionization stage of mass spectrometry analysis, including the $MS^1$ ionization stage of MS/MS analysis. As used herein, the term "product ion" is to refer to an ion which is produced during a fragmentation process of a precursor ion, such as the $MS^2$ fragmentation stage of MS/MS analysis.

The terms "peptide" and "polypeptide" are used synonymously in the present description, and refer to a class of compounds composed of amino acid residues chemically bonded together by amide bonds (or peptide bonds). Peptides and polypeptides are polymeric compounds comprising at least two amino acid residues or modified amino acid residues. Modifications can be naturally occurring or non-naturally occurring, such as modifications generated by chemical synthesis. Modifications to amino acids in peptides include, but are not limited to, phosphorylation, glycosylation, lipidation, prenylation, sulfonation, hydroxylation, acetylation, methylation, methionine oxidation, alkylation, acylation, carbamylation, iodination and the addition of cofactors. Peptides include proteins and further include compositions generated by degradation of proteins, for example by proteolyic digestion. Peptides and polypeptides can be generated by substantially complete digestion or by partial digestion of proteins. Polypeptides include, for example, polypeptides comprising 1 to 100 amino acid units, optionally for some embodiments 1 to 50 amino acid units and, optionally for some embodiments 1 to 20 amino acid units.

Antibodies are specialized proteins produced by the immune system as a defense against foreign agents (antigens). Each antibody has a region that binds specifically to a particular antigen which it neutralizes.

Antibody Drug Conjugates (ADCs) are monoclonal antibodies (mAbs) attached to biologically active drugs by chemical linkers with labile bonds. The antibody region is preferably selective for an antigen expressed on cells or tissues to which the biologically active drug is designed to be delivered. For example, the antibody region may be selective for a tumor-associated antigen that has restricted or no expression on normal (healthy) cells and therefore enables the ADC to deliver the biologically active drug to the tumor cells.

Therapeutic proteins can be any protein, fusion protein, or polypeptide isolated or produced for pharmaceutical use. Therapeutic proteins include, but are not limited to, anticoagulants, blood factors, bone morphogenetic proteins, engineered protein scaffolds, enzymes, growth factors, hormones, interferons, interleukins, and thrombolytics. Therapeutic proteins can also be classified based on their molecular mechanism of activity as (a) binding non-covalently to target, e.g., mAbs; (b) affecting covalent bonds, e.g., enzymes; and (c) exerting activity without specific interactions, e.g., serum albumin.

K-means clustering analysis is a commonly used data clustering process for unsupervised learning tasks (see, for example, Hartigan and Wang, 1979, "A K-means clustering algorithm," Applied Statistics 28: 100-108; and. J. B. MacQueen, 1967, "Some Methods for classification and Analysis of Multivariate Observations, Proceedings of 5th Berkeley Symposium on Mathematical Statistics and Probability", Berkeley, University of California Press, 1:281-297). K-means clustering can be used to find groups which have not been explicitly labeled in the data.

Overview

As described herein, mass spectrometry can be used to detect peptides that are created by digesting proteins, either purified protein or complex mixtures of proteins, into smaller, easier to detect peptide samples. The samples are typically separated via liquid chromatography after which the peptides are ionized and injected into the mass spectrometer where they are separated based on the mass to charge ratio (m/z) during the $MS^1$ stage. A selected set of ions are subsequently fragmented and separated during the $MS^2$ stage, the result of which is a "fingerprint" that is used to identify the protein via a comparative database search. This process, known as shotgun proteomics, has become the primary method for protein detection and quantification.

Because of incomplete digestion, typically only a fraction of the peptides from the parent protein are actually detected and analyzed. Many modifications, splicing events, single nucleotide polymorphisms, and truncations of the proteome frequently occur and are tightly regulated. However, because the entire protein sequence is not detected, it is often impossible to determine whether the expressed protein is present in a modified, spliced, or truncated form.

To overcome these limitations, the present invention provides methods and systems for analyzing polypeptides which provide increased sequence coverage and improved analysis. Aspects of the present invention provide a sequencing strategy to provide more protein sequence coverage than is typically achieved, and a computational approach to view a proteins expression across its full length and identify regions of the protein that are potentially subject to such regulation. This technology has global utility in any proteomics experiment and will be of particular use for the analysis of biosimilar protein drug therapeutics.

Examples

In a first example, a large scale study of the yeast proteome was performed. The proteome was digested with the following six proteases: trypsin, Lys-N, Lys-C, Glu-C, chymotrypsin, and Asp-N. Over 6,000 proteins (95% of the yeast proteome) were identified with a mean sequence coverage of 80%. To enable the identification of endogenous peptides produced by natural proteolytic activity in the cell, the data was processed with a no enzyme search. Of special interest was the mitochondrial proteome, most of which is subject to N-terminal processing of the full protein sequence. The well characterized coenzyme Q5 (COQ5) protein, a methyltransferase, essential to the ubiquinone biosynthesis pathway, was selected. COQ5 undergoes post-translational processing by N-terminal truncation. FIG. 1 illustrates the sequencing depth of COQ5, with over 250 quantified peptides.

Figure 2:
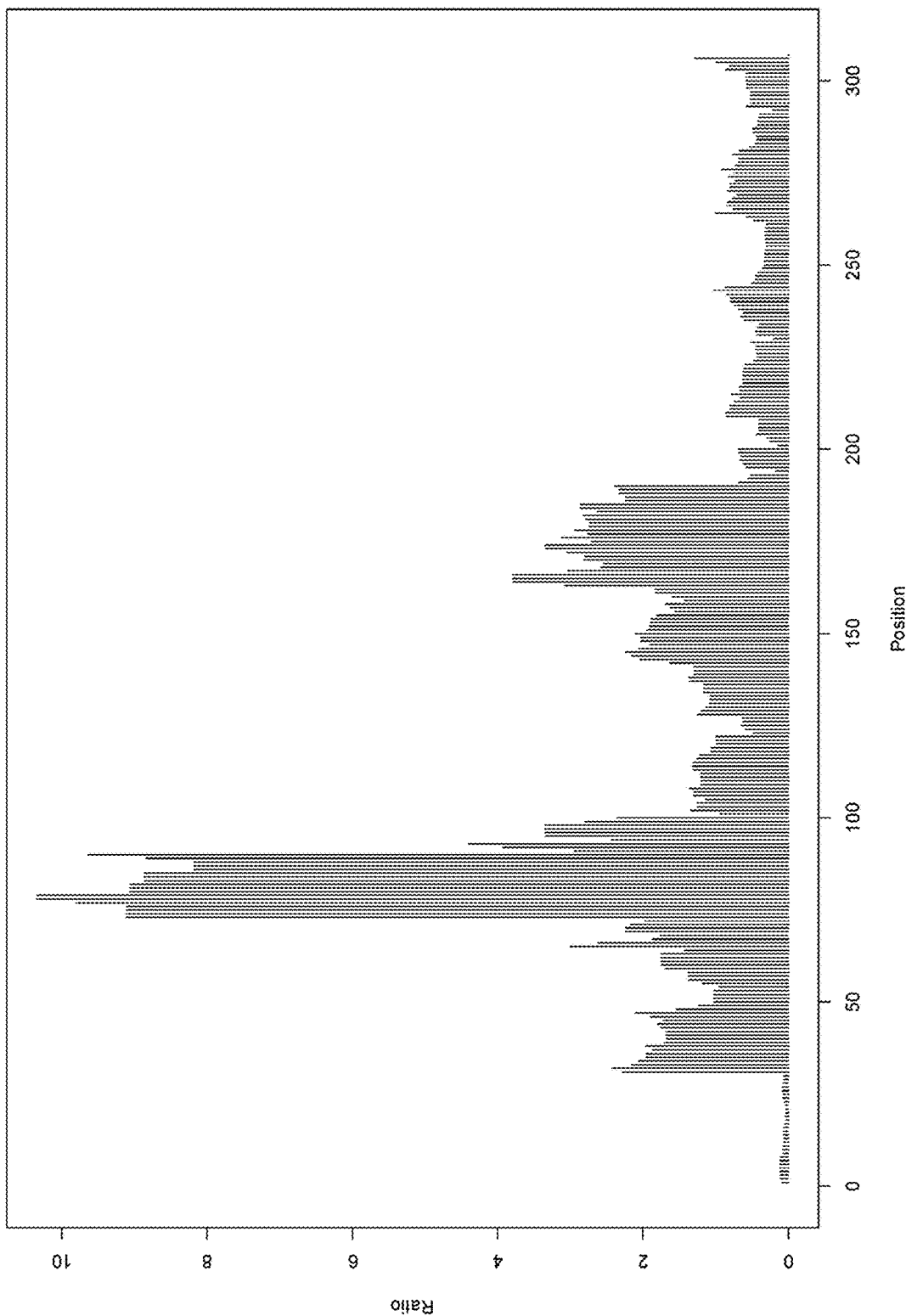
FIG. 2 shows an amino acid consensus map of coenzyme Q5. Each bar represents the ratio of the normalized amino acid intensity to the median amino acid intensity over the full sequence length of coenzyme Q5. The N-terminal region corresponds to a transit peptide.

The peptide mapping reveals the dynamic range of peptides from multiple proteases, but also putative proteoforms. To distinguish features unique to proteoforms, e.g., truncation or PTM sites, an amino acid consensus map was built by grouping the peptide information to distinguish features unique to proteoforms, such as truncation or PTM sites. In doing so, peptide intensities were normalized to adjust bias in protease activity and ionization efficiency over proteases (FIG. 2). To distinguish technical from biological variability, a test statistic was implemented to assign significance to variability in amino acid intensities.

With this method, the N-terminal processed proteoform (amino acid position 31) was able to be distinguished from the unprocessed proteoform (FIG. 2) of COQ5.

This method enables the detection of proteoforms not readily accessible in a typical shotgun proteomics experiment. This example is one of many for N-terminal truncation, but other proteoform features, such as alternative gene products, PTM sites, and sequence variations, are also able to be distinguished. This is a use case, which requires a single condition, but it would be easy to extend the method to multiple conditions. Such a comparative analysis, e.g., between control and treatment sample(s) would allow to identify changes in proteoform composition and respective features.

In addition, the use of multiple proteases overcomes a limitation of common shotgun proteomic techniques that rely heavily on trypsin. Cleavage with trypsin at amino acids arginine and lysine results in a mean protein sequence coverage of 15% to 20%. While sufficient for most proteomics experiments, the limited coverage does not allow for the identification of individual proteoforms. The mixture of six proteases increases the mean sequence coverage to 80%, and when combined with the bioinformatic analysis, allows for the identification of putative proteoforms with unprecedented amino acid resolution.

Methods

Yeast Culture and Lysis. *Saccharomyces cerevisiae* strain BY4741 was grown in yeast extract peptone dextrose media (1% yeast extract, 2% peptone, 2% dextrose). Four liters of media was divided between four two-liter flasks and inoculated with a starter culture (OD600=1.17). Cells were allowed to propagate for ~18 h to an average OD600 of 1.31. The cells were harvested by centrifugation at 5000 rpm for 5 min, the supernatant was decanted, and the pellets were resuspended in chilled NanoPure water. The cells were washed two more times and centrifuged for the final pelleting at 5000 rpm for 10 min. A pellet corresponding to 5% of the total cells grown was resuspended in lysis buffer containing 8 M urea, 50 mM tris (pH 8), 75 mM sodium chloride, 100 mM sodium butyrate, protease (Roche) and phosphatase inhibitor tablet (Roche). Yeast cells were lysed by glass bead milling (Retsch). Briefly, 2 ml of acid washed glass beads were combined with 2.5 ml of resuspended yeast cells in a stainless steel container and shaken 8 times at 30 Hz for 4 min with a 1 min rest in between. Lysate protein concentration was measured by BCA (Thermo Pierce).

Digestion. Protein was reduced by addition of 5 mM dithiothreitol and incubated for 45 min at 55° C. The mixture was cooled to room temperature, followed by alkylation of free thiols by addition of 15 mM iodoacetamide in the dark for 30 min. The alkylation reaction was quenched with 5 mM dithiothreitol. For tryptic digestion, a 1 mg protein aliquot was digested overnight with 20 μg trypsin (Promega, Madison, WI) at room temperature in 1 M urea. For LysC digestion, a 1 mg protein aliquot was digested overnight with 20 μg LysC (Wako, Richmond, VA) at room temperature in 4 M urea. For LysN digestion, a 1 mg protein aliquot was digested for four hours with 20 μg LysN (Thermo Pierce) at 37° C. in 4 M urea. For GluC digestion, a 1 mg protein aliquot was digested overnight with 25 μg GluC (Roche Diagnostics, Indianapolis, IN) at room temperature in 0.5 M urea. For chymotrypsin digestion, a 1 mg protein aliquot was digested overnight with 12.5 μg of chymotrypsin resuspended in 0.2% FA (Promega, Madison, WI) in 1 M urea. For digestion with AspN, a 1 mg protein aliquot was incubated with 6 μg AspN (Roche Diagnostics, Indianapolis, IN) at room temperature overnight. Each digest was quenched by the addition of TFA and desalted on a 100 mg C18 Sep-Pak cartridge (Waters, Milford, MA).

Fractionation. High-pH RP fractionation was performed using a Surveyor LC quarternary pump. Fractionation was performed at a flow rate of 1.0 mL/min using a 5 μm column packed with C18 particles (250-mm by 4.6-mm, Phenomenex) on a Surveyor LC quarternary pump. Samples were resuspended in buffer A and separated using the following gradient: 0-2 min, 100% buffer A and separated by increasing buffer B over a 60-minute gradient at a flow rate of 0.8 mL/minute (buffer A: 20 mM ammonium formate, pH 10; buffer B: 20 mM ammonium formate, pH 10, in 80% ACN). Flow rate was increased to 1.5 mL/minute during equilibration. Peptides were concatenated to a final total of twenty fractions per enzymatic digest.

LC-MS/MS. Samples were resuspended in 0.2% formic acid (FA) and separated via reversed phase (RP) chromatography. Peptides were injected on to a RP column prepared in-house. Approximately 35 cm of 75 μm-360 μm inner-outer diameter bare-fused silica capillary, each with a laser pulled electrospray tip, were packed with 1.7 μm diameter, 130 Å pore size, Bridged Ethylene Hybrid C18 particles (Waters). Columns were fitted on to either a nanoAcquity (Waters) or Dionex (Thermo) and heated to 60° C. using a home-built column heater. Mobile phase buffer A was composed of water and 0.2% formic acid. Mobile phase B was composed of 70% ACN, 0.2% formic acid, and 5% DMSO. Each sample was separated over a 100-min gradient, including time for column re-equilibration. Flow rates were set at 300-350 μl/min.

Peptide cations were electrosprayed into a Thermo Orbitrap Fusion (Q-OT-qIT, Thermo). All fractions were analyzed using HCD and ETD. For HCD, precursor scans were performed from 300 to 1,500 m/z at either 60K or 120K resolution (at 400 m/z). A $5\times10^5$ ion count target was used. Precursors selected for tandem MS were isolated at 0.7 Th with the quadrupole, fragmented by HCD with a normalized collision energy of 30, and analyzed using turbo scan in the ion trap. The maximum injection time for $MS^2$ analysis was normally set at either 25 or 35 ms, but was set higher for some analyses, with an ion count target of 104. Precursors with a charge state of 2-8 were sampled for $MS^2$. Dynamic exclusion time was set at 15 seconds, with a 10 ppm tolerance around the selected precursor and its isotopes. Monoisotopic precursor selection was turned on. Analyses were performed in top speed mode with either 3 or 5 second cycles.

To maximize identifications from ETD analysis, precursor scans were performed from 200 to 800 m/z at either 60K or 120K resolution (at 400 m/z). A $5\times10^5$ ion count target was used on the Orbitrap Fusion, a $1\times10^6$ ion count target was used on the Orbitrap Lumos. Precursors selected for tandem MS were isolated at 0.7 Th with the quadrupole. Precursors were fragmented by ETD using custom reaction times; +3: 40 ms, +4: 22 ms, +5: 14 ms, +6: 10 ms, +2: 70 ms. EThcD was performed on +2 precursors, at 25% supplemental activation collision energy. Precursor ions were selected for fragmentation based on charge state in the following order: +3, +4, +5, +6, +2. Fragment ions were analyzed in the ion trap. Dynamic exclusion time was set at 15 seconds, with a 10 ppm tolerance around the selected precursor and its isotopes. Monoisotopic precursor selection was turned on. Analyses were performed in top speed mode with either 3 or 5 second cycles.

Data Processing and Bioinformatics Analysis. The raw mass spectrometry data was processed using the MaxQuant software (version 1.5.7.5). Searches were performed against the UniProt database (UP000002311_559292). Searches were conducted using the default precursor mass tolerances set by *Andromeda* (20 ppm first search, 4.5 ppm main search) and product mass tolerance of 0.35 Da and 0.015 Da, respectively. A maximum of two missed tryptic cleavages was allowed. The fixed modification specified was carbamidomethylation of cysteine residues. The variable modifications specified were oxidation of methionine and protein acetylation (N-term). For all experiments, peptides and their corresponding proteins groups were both filtered to a 1% false discovery rate.

The peptide extracted-ion chromatogram (XIC) intensities from the MaxQuant peptides file were used. The XIC intensities were normalized by quantile normalization. To construct the amino acid map the peptide sequences were assembled to the reference sequences provided in the protein sequence database. Amino acid abundances were calculated as the mean of the XIC peptide intensities matching to the amino acid position in the protein sequence. A ratio for each amino acid was calculated by dividing the abundance by the median abundance. The ratios were used in one or two sample T-tests (requires replicate analysis) to infer statistical significance for each amino acid position. To control Type I errors a multiple hypothesis test correction (FDR) was performed.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components or compounds is disclosed herein, it is understood that all individual members of those groups and all subgroups thereof are disclosed separately. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements.

One of ordinary skill in the art will appreciate that starting materials, device elements, analytical methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein. Headings are used herein for convenience only.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

The invention claimed is:

1. A method for analyzing a polypeptide having an amino acid sequence comprising the steps of:
   a) obtaining a first and second sample of the polypeptide from one or more cells;
   b) digesting the first sample of the polypeptide with a first protease or chemical agent;
   c) digesting the second sample of the polypeptide with a second protease or chemical agent;
   d) generating tandem mass spectrometry data on each digested polypeptide sample comprising the steps of:
   generating a distribution of precursor ions during MS1 stage ionization,
   fragmenting precursor ions having a mass-to-charge ratio (m/z) within a selected target m/z range during MS2 stage fragmentation, thereby generating a plurality of product ions wherein the product ions correspond to portions of the amino acid sequence of the polypeptide,
   measuring m/z of the product ions,
   obtaining peptide extracted-ion chromatogram (XIC) intensities of the product ions from each digested polypeptide sample, and
   normalizing the measured XIC intensities of the product ions using quantile normalization, thereby generating normalized mass spectrometry data for each digested polypeptide sample;
   e) combining the normalized mass spectrometry data from each digested polypeptide sample, wherein the normalized mass spectrometry data comprises at least the normalized XIC intensities for each digested polypeptide sample, thereby generating comprehensive mass spectrometry data on the polypeptide, wherein the comprehensive mass spectrometry data provides sequence coverage for at least 50% of the full length amino acid sequence of the polypeptide; and
   f) identifying a portion of the product ions as corresponding to one or more known amino acid sequence fragments of said polypeptide, and calculating abundances of amino acids for one or more selected portions of the polypeptide from the comprehensive mass spectrometry data, wherein a ratio for an amino acid within the one or more selected portions of the polypeptide is calculated by dividing the mean abundance of the amino acid from the normalized XIC intensities by a median abundance of amino acids across the polypeptide.

2. The method of claim 1 further comprising generating at least a partial consensus amino acid sequence for the polypeptide from the comprehensive mass spectrometry data, and identifying post-translational modification (PTM) sites in the amino acid sequence for the polypeptide.

3. The method of claim 2 comprising comparing normalized mass spectrometry data for each digested polypeptide sample to determine differences in PTMs of amino acids between each sample.

4. The method of claim 1 wherein the one or more selected portions comprises the N-terminus of the polypeptide.

5. The method of claim 1 further comprising normalizing the measured intensities of the product ions to adjust for bias in protease activity and ionization efficiency.

6. The method of claim 1 further comprising performing k-means clustering analysis on normalized XIC intensity data during generation of the normalized mass spectrometry data.

7. The method of claim 1 further comprising digesting one or more additional samples of the polypeptide with one or more additional proteases or chemical agents, wherein the protease or chemical agent used for each sample is a different protease or chemical agent used to digest any other sample.

8. The method of claim 7 further comprising digesting a third sample of the polypeptide with a third protease, digesting a fourth sample of the polypeptide with a fourth protease, digesting a fifth sample of the polypeptide with a fifth protease, and digesting a sixth sample of the polypeptide with a sixth protease.

9. The method of claim 7 wherein the proteases or chemical agents are proteases selected from the group consisting of trypsin, Lys-N, Lys-C, Glu-C, chymotrypsin, Asp-N, and combinations thereof, wherein each selected protease is different for each sample.

10. The method of claim 1 wherein the comprehensive mass spectrometry data provides sequence coverage for at least 60% of the full length amino acid sequence of the polypeptide.

11. The method of claim 1 wherein the comprehensive mass spectrometry data provides sequence coverage for at least 80% of the full length amino acid sequence of the polypeptide.

12. The method of claim 1 wherein the polypeptide is an antibody, antibody-drug conjugate, or a therapeutic protein.

* * * * *